United States Patent [19]

Eiseman

[11] 4,231,781
[45] Nov. 4, 1980

[54] HALOPHENOXY-ALKOXY PHOSPHONATES AND THIOPHOSPHONATES

[75] Inventor: Fred S. Eiseman, Basking Ridge, N.J.

[73] Assignee: GAF Corporation, New York, N.Y.

[21] Appl. No.: 938,376

[22] Filed: Aug. 31, 1978

[51] Int. Cl.³ .................. A01N 57/10; C07F 9/12; C07F 9/18
[52] U.S. Cl. ........................ 71/87; 260/924; 260/947; 260/948; 260/951; 71/86
[58] Field of Search ............. 260/924, 947, 948, 951; 71/87

[56] References Cited
U.S. PATENT DOCUMENTS 3,247,134  4/1966  Hwa et al. .................. 260/924 X

*Primary Examiner*—Anton H. Sutto
*Attorney, Agent, or Firm*—Walter C. Kehm; Marilyn J. Maue

[57] ABSTRACT

The halophenoxy-alkoxy phosphonates and corresponding thiophosphonates of the present invention are represented by the general formula:

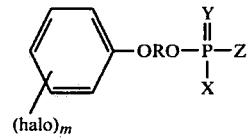

wherein
R is alkylene having from 1 to 4 carbon atoms;
Y is O or S;
X is —OH, halo,

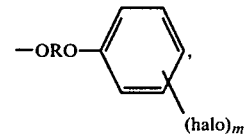

,—ORSROH, or —OH.N4R′″(ROH);
Z is —OH, halo,

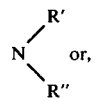

when X is —OH.N4R′″(ROH), then Z can also be —OH.N4R′″(ROH);
R′ is H or alkyl having from 1 to 4 carbon atoms;
R″ is $C_{1-4}$ alkyl sulfonic acid or a salt thereof, such as the halide or alkali metal salt;
R′″ is H or —ROH; and
m is an integer from 1 to 5
and wherein at least one of X and Z is other than —OH. These compounds are particularly useful as pre-emergent herbicides and lubricants or lubricant additives.

11 Claims, No Drawings

HALOPHENOXY-ALKOXY PHOSPHONATES AND THIOPHOSPHONATES

The present invention relates to novel compounds having herbicidal activity on weeds such as chickweed, lambsquarter, quackgrass, bindweed, etc. The present compounds are also useful lubricants for gears and other metal working parts.

The halophenoxy-alkoxy phosphonates and thiophosphonates of this invention are described by the formula:

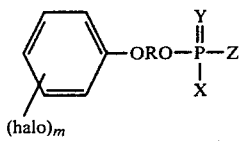

wherein
R is alkylene having from 1 to 4 carbon atoms;
Y is O or S;
X is —OH, halo,

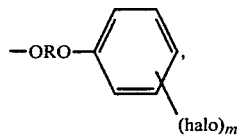

—ORSROH, or —OH.NH(R''') (ROH);
Z is —OH, halo,

when X is —OH.NH(R''') (ROH); then Z can also be —OH.NHR'''(ROH);
R' is H or alkyl having from 1 to 4 carbon atoms;
R'' is $C_{1-4}$ alkyl sulfonic acid or a salt thereof, such as halide or alkali metal salt;
R''' is H or —ROH; and
m is an integer from 1 to 5;
and wherein at least one of X and Z is other than —OH.

Specific examples of the present compounds include chlorinated, brominated, fluorinated, or iodinated phenoxy-alkoxy thiophosphonic acids, or said halogenated phenoxy-alkoxy phosphate- and thiophosphonate-esters, sulfides and amines such as dichlorophenoxyethoxy thiophosphonic acid monoethylamine; dichlorophenoxy-ethoxy thiophosphonic monoalkylsulfonic acid amine, the corresponding bromide or chloride salt of the sulphonic acid amine or the corresponding sodium or potassium salt of the sulfonic acid amine; the monoethanol diamine salt of dichlorophenoxyethoxy-thiophosphonic acid and the corresponding salt of phosphonic acid; bis(trichlorophenoxyethoxy)thiophosphonic acid ester; bis(dichlorophenoxyethoxy)phosphonic acid ester; dichlorophenoxypropoxy thiophosphonic acid; the P-dichlorophenoxyethoxy-P-diethanol sulfide ester of phosphonic acid; the P-perchlorophenoxyethoxy-P,P-bis(N-methyl taurine chloride) of phosphonyl chloride; P-bromo-phenoxypropoxy-P-taurine salt of phosphonyl chloride; the diethanol monoamine adduct of trichlorophenoxyethoxy phosphonic acid; the monoethanol diamine adduct of dichlorophenoxyethoxy phosphonic acid; the dimethyl amine salt of dichlorophenoxyethoxy phosphonic acid; P-dichlorophenoxybutoxy-P,P-bis(sodium taurate) of phosphonyl chloride; P-chlorophenoxypropoxy-P-(N-potassium taurate) of phosphonyl chloride; difluorophenoxyethoxy phosphonyl dichloride; P,P-bis(dibromophenoxyethoxy) phosphonyl monochloride; the ethylamine salt of dichlorophenoxy ethoxy phosphonic acid, etc. Of this group, the dichlorophenoxyethoxy phosphorous-containing compounds are preferred.

The compounds of this invention may be conveniently prepared by reacting a halophenoxyalkanol with phosphoric acid, thiophosphoric acid, a mixture of polyphosphoric and hypophosphorous acids, or the thio derivatives of said mixture of acids, to provide the corresponding halophenoxyalkoxy phosphonic acid or the corresponding halophenoxyalkoxy thiophosphonic acid or the ester derivatives of this invention. These acids or ester derivatives can then be further reacted with an alkanol amine, a dialkanol sulfide or an alkyl sulfonic acid amine or a halide or alkali metal salt thereof to produce the corresponding sulfide or amino derivative or amino adduct. The following generic equation (II) covers the general reactions for the preparation of the compounds of the present invention.

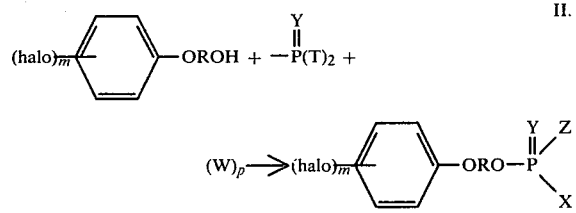

wherein
p has a value of 0 or 1;
W is —NR'''(ROH), HOR—S—ROH or

T is OH or halogen and m, R', R'', R''', halo, X, Y and Z have the same meaning as in Formula I. Specific preparations for various groups of products embraced by Equation II are as follows:

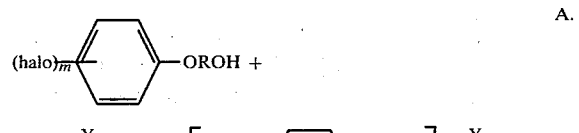

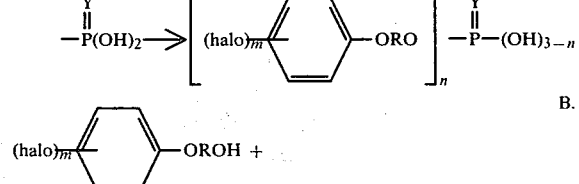

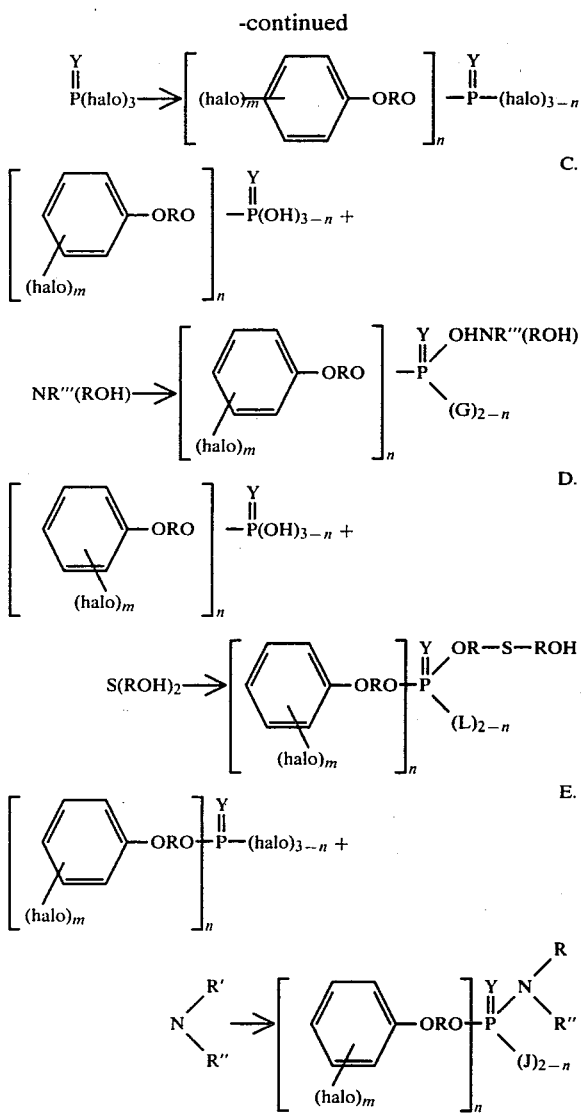

wherein
G is —OH or —OH-NH(R''') (ROH);
L is —OH or —OR—S—ROH amd J is halo or

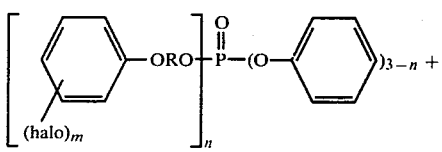

and halo, m, R, R', R'', R''' and Y are the same as in Formula I.

Alternatively, the thioether substiuted phosphonate can be prepared by reacting a halophenoxyalkoxyphenoxy phosphonate with the above dialkanol sulfide, i.e.

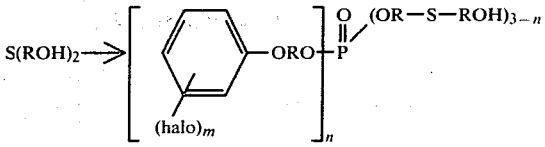

The corresponding thiophosphonate can also be prepared by reacting sulfur, preferably in the form of a powder, with the phosphonate product of reaction D or F whereupon substitution of the oxygen doubly bonded to phosphorous with sulfur takes place.

The aforementioned reactions are generally effected at a temperature between about 30° C. and about 150° C. under a pressure of from about 10 psig to about 100 psig; preferably at a temperature between about 50° C. and about 100° C. under atmospheric or ambient pressure. The reactions are allowed to take place over a period of from about 0.5 to about 20 hours, depending upon the severity of the reaction conditions. Stoichiometric amounts of the reactants are employed, although up to about a two-fold excess over stoichiometry of the halogenated phenoxyalkanol can be employed if desired.

For best results, it is recommended that the reaction mixture be constantly agitated and that the phosphorous-containing reactant be added to the halophenoxy alkanol prior to reaction or introduced intermittantly during reaction. Alternatively, a mixture of these reactants can be introduced simultaneously into the reactor and the reaction carried out, with agitation, in a closed or open system. The reaction may be effected in the absence or in the presence of a solvent such as benzene, toluene, xylene, cyclohexane, or any other inert organic liquid preferably of the paraffin series.

By selection of the particular phenoxylkanol employed in the preparation, the value of n and R can be varied. Representative of the phenoxy alkanols which may be employed are:
2,3, or 4-chlorophenoxy methanol
2,3, or 4-chlorophenoxy ethanol
2,3, or 4-chlorophenoxy propanol
2,3, or 4-chlorophenoxy butanol
2,4-, 3,4- or 2,3-dichlorophenoxy methanol
2,4-,3,4- or 2,3-dichlorophenoxy ethanol
2,4-, 3,4- or 2,3-dichlorophenoxy propanol
2,4-3,4-2,3-dichlorophenoxy butanol
2,3,4-trichlorophenoxy ethanol
2,3,4-trichlorophenoxy propanol
2,3,4-trichlorophenoxy butanol
perchlorophenoxy methanol
perchlorophenoxy ethanol
perchlorophenoxy propanol
2,3,4,6-tetrachlorophenoxy ethanol, etc.
and the corresponding fluoro-, bromo- or iodo- derivatives of the above compounds.

Suitable examples of alkanol amine reactants include mono- and dimethanol amines, mono- and di- ethanol amines, mono- and di- propanol amines and mixtures thereof.

Examples of dialkanol sulfides which may be reacted with the phosphonic acid esters of the present invention include dimethanol sulfide, diethanolsulfide, dipropanol sulfide, dibutanol sulfide, methanol ethanol sulfide, ethanol propanol sulfide and mixtures thereof.

Illustrative of the sulfonic acid amines and salts thereof which may be reacted with the present phosphonyl halide esters of this invention include taurine, aminopropyl sulfonic acid, aminobutylsulfonic acid, N-methyl taurine, N-ethyl taurine, N-methyl-N-propyl amino sulfonic acid, N-methyl-N-butyl amino sulfonic acid and mixtures thereof, and the corresponding sulfonic fluorides, chlorides, bromides, or iodides of these compounds or the corresponding sodium, potassium or lithium sulfonic acid salts of these compounds.

Reference is now had to the following examples which illustrate preferred embodiments, but which are not to be construed as limiting to the scope of this invention as defined in the foregoing disclosure and in the accompanying claims.

EXAMPLE I

To a 500 ml flask, 310 grams of 2,4-dichlorophenoxy ethanol and 2 grams of hypophosphorous acid are charged and the contents agitated at room temperature. The mixture is heated to 40°-45° C. and 255 grams of 115% polythiophosphoric acid is gradually added over a period of one hour, after which the flask is slowly heated up to 90°-95° C. and held at that temperature for an additional 4 hours. The orange colored product, a mixture of mono- and di- esters of the following formulae, solidified when cooled to room temperature.

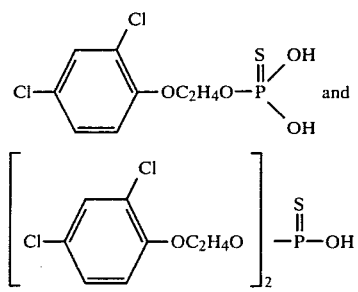

The product, is obtained in 45% yield and the ratio of monoester to diester is about 1.3:1. It is to be understood that the corresponding mono-, di or tri-chlorophenoxy alkanol (e.g. methanol, ethanol, propanol or butanol) as well as the corresponding fluoro-, bromo- or iodo-derivatives of these compounds can be substituted in instant example to provide the corresponding products.

EXAMPLE II

To 200 grams of the above monoester in 300 ml of water is added 260 grams of diethanol amine until a pH of 7.0 is obtained. After agitating the mixture for four hours at 50° C., a solid product, having the formula:

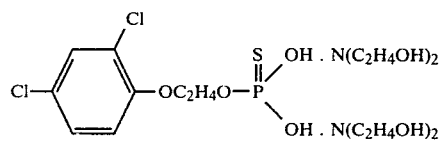

is obtained in about 40% yield.

In this example, the corresponding diester reactant can be substituted for the monoester to provide the corresponding mono amino adduct. Similarly, any of the other mono- or di- alkanol amines, such as, e.g. monoethanol amine, monopropanol amine, monobutanol amine, dimethanol amine, dipropanol amine, etc. can be substituted as a reactant in instant example to provide the corresponding substituted thiophosphonic acid amino adduct.

EXAMPLE III

A. Example I is repeated except that hypophosphorous acid is substituted for hypothiophosphorous acid and polyphosphoric acid is substituted for polythiophosphoric acid. The monoester, having the formula:

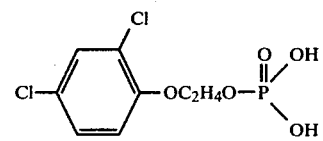

is recovered and reacted with diethanol amine as in Example II to give a light colored solid product having the formula:

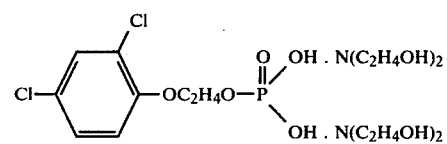

B. It is to be understood that in the present example the corresponding diester starting material can be substituted so that a product having the general formula:

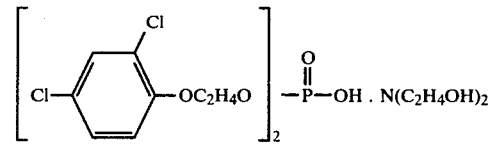

is obtained.

C. Also, when the monoester of either Example I or the present example is employed and only about 75-100 grams, in place of 260 grams, of the diethanol amine is added thereto, the primary product obtained has the formula:

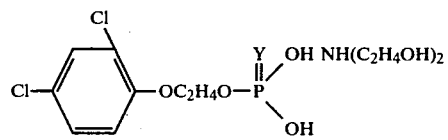

where Y is sulfur or oxygen.

It is to be understood that any of the other amino derivatives referred to in Example II and recited heretofore or any of the other halophenoxy alkanols referred to in Example I and mentioned heretofore, can be substituted as reactants in the above to provide the corresponding amino derivatives of the compounds discussed above.

EXAMPLE IV

A sealed glass flask is charged with 200 grams of 2,4-dichlorophenoxy ethanol and 77 grams of POCl₃ is added thereto with constant agitation at a temperature of 40°-50° C. over a period of 1.25 hours. The mixture is then heated to 65°-70° C. at which temperature the reaction mixture is agitated for 0.5 hour. A compound,

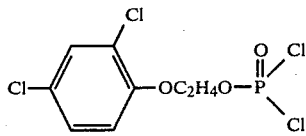

is formed. N-methyltaurine is then added with stirring to the reactor while nitrogen is bubbled through the mixture for one hour at 65°–70° C. After an additional 15 minutes the mixture is allowed to cool and a product having the formula:

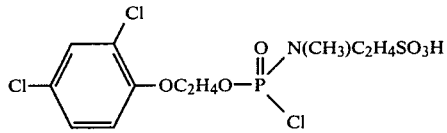

is recovered in about 40% yield. A minor amount of a secondary product having the formula:

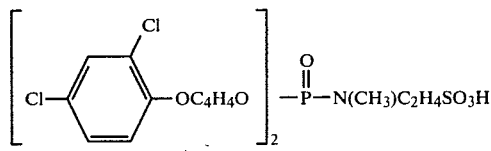

is also obtained.

It is to be understood that in this example, the halide salt of the alkyl sulfonic acid amine e.g. the chloride, fluoride, bromide or iodide salt of taurine, can be substituted in the above reaction with the above named, or other halophenoxyalkoxy-phosphonyl chloride to provide the corresponding halosubstituted taurine salts of the products illustrated.

EXAMPLE V

Into a glass autoclave is charged 194 grams of bis(2,4-dichlorophenoxyethanol) phosphonic acid chloride, 194 grams of the sodium salt of N-methyltaurate in a 31% aqueous solution, 35 grams of NaOH and 300 ml of water. The mixture is agitated at room temperature and 30% aqueous sodium hydroxide is added to maintain the pH within the range of 10.5 to 11.0, after which the pH is adjusted to 9.0 with HCl. The product was obtained as a white solid having the formula:

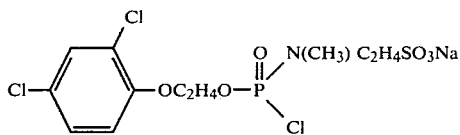

and in about 75.5% conversion.

In the above example, either the potassium or lithium salt of taurine can be substituted for the sodium salt to produce the corresponding salt product.

EXAMPLE VI

Into a glass autoclave is added 226 grams of thiodiethanol, 300 grams of P-(2,4-dichlorophenoxyethoxy)-phosphate monoester and 2.5 grams of hypophosphorous acid. The components are constantly agitated at room temperature for one hour, after which 200 grams of polyphosphoric acid is added gradually over a period of one hour at a temperature of 40°–45° C. After the addition is complete, the mixture is heated for four hours to between 90° and 95° C. The product:

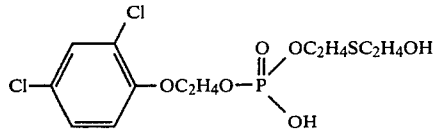

formed in about 50% yield solidifies upon cooling and is recovered as a light solid. The product is then treated with 13 grams of powdered sulfur in aqueous solution at a temperature of between 130° and 135° C. for about one hour, after which the product is cooled and solidified to a light solid having the following formula:

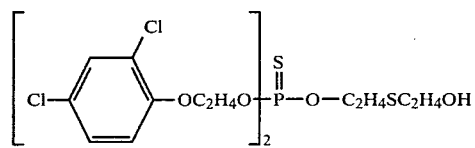

EXAMPLE VII

Into a 500 ml flask is added 300 grams of 2,4-dichlorophenoxy ethanol and 250 grams of the chloride salt of taurine with continuous stirring at a temperature of 40°–45° C. It is to be understood that the corresponding fluoride or bromide of taurine can replace said chloride to produce the corresponding taurine fluoride or bromide salt derivative. After about 1.0 hour, 77 grams of phosphoryl chloride is added dropwise to the mixture over a period of 1.25 hours and the temperature is held at 40°–45° C. Upon completion of the addition, the temperature of the mixture is raised to 65°–70° C. and agitated for 0.5 hour. Nitrogen is then bubbled through the mixture for one hour at the same temperature. The product is then allowed to cool to room temperature and then is recovered by filtration as a light colored solid. About 75.5% conversion to product having the formula:

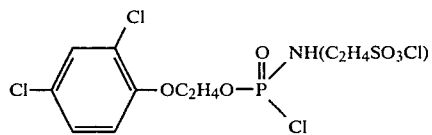

is obtained.

It is to be understood that, in the above examples, any of the other halophenoxy alkanols heretofore mentioned, e.g. the mono-, di-, tri-, tetra- or per-, chloro-, bromo- or fluoro- phenoxy alkanols can be substituted to provide the corresponding phosphate or thiophosphate derivatives. Specific examples of the halophenoxy ethanols which may be employed include 2,4-di-bromophenoxy propanol, 2,4-difluorophenoxy ethanol, perchlorophenoxyethanol, etc.

When the compounds of the present invention are employed as herbicides they are mixed with a liquid or particulate solid carrier or extender which is inert with respect to the present herbicide. Examples of suitable carriers include water, hydrocarbon alkanes of from 4 to 10 carbon atoms, benzene, xylene, toluene, a mineral oil fraction, a vegetable oil, etc. The concentration of the herbicide in the carrier is between about 200 ppm and about 15,000 ppm; preferably between about 1,000 ppm and about 10,000 ppm. Ther herbicide is applied to a plant or plant situs at 0.2 to 20 grams per hectare. The present herebicides, when applied to the pre-emergent plant situs prevents emersion of chickweed and controls noxious weeds such as for example chickweed, lambsquarter when applied to growing plants.

EXAMPLE VIII

When an aqueous solution containing about 5,000 ppm of the herbicidal agents of this invention is applied at about 8 lbs/acre to a field wherein mustard and pigweed are growing with wheat, rye, oats or barley, 65 to 85% of the mustard and pigweed undergo severe injury while the graminae crop is practically uneffected.

More complete control is realized when the field is treated before sprouting of the weed. Particularly active agents are:

$$[Cl-C_6H_3(Cl)-OCH_2CH_2O]_2-P(=O)-N(CH_3)(CH_2CH_2SO_3H),$$

$$[Cl-C_6H_3(Cl)-OCH_2CH_2O]_2-P(=O)-OCH_2CH_2SCH_2CH_2OH,$$

$$[Cl-C_6H_3(Cl)-OCH_2CH_2O]_2-P(=S)-OCH_2CH_2SCH_2CH_2OH,$$

and $$Cl-C_6H_3(Cl)-OCH_2CH_2O-P(=O)(OH)(OH \cdot NH(C_2H_4OH)).$$

EXAMPLE IX

A. Into a glass autoclave is added 122 grams of thiodiethanol and 536 grams of bis(phenoxy)-4-chlorophenoxyethoxy phosphonate, obtained from condensation of excess phenol with P-(4-chlorophenoxyethoxy) phosphonic acid.

The mixture is agitated for about 0.75 hour at an initial reaction temperature of 120° C. gradually increasing to 212° C. under a pressure of about 10 mm. The product:

$$Cl-C_6H_4-OCH_2CH_2O-P(=O)-(O-CH_2CH_2SCH_2CH_2OH)_2$$

is separated by distillation as a light yellow liquid boiling at about 220° C.

B. The above product (156 grams) is added to a glass autoclave containing 13 grams of powdered sulfur and the mixture heated slowly to 130°-135° C. over a period of 0.75 hour. The light colored product:

$$Cl-C_6H_4-OCH_2CH_2O-P(=S)-(OCH_2CH_2SCH_2CH_2OH)_2$$

solidified on cooling to room temperature.

The products of the present invention, when employed in aqueous solutions, for example of between about 0.01% and about 1% concentration, may be employed as antiwear agents and lubricants for heavy machinery. Aqueous solutions containing up to about 10% of the above products are also useful as agricultural chemicals, applied to the soil at a rate of between about 1 and about 20 pounds per acre, e.g. as a weed preventative and herbicide. Still further they are generally useful as oil additives in cutting oils, mineral lubricating oils of petroleum origin and synthetic lubricants. The present products also find application as greases, rust preventatives, etc.

Many modifications and variations of the present invention will become apparent from the above disclosure, however, it is to be understood that these are also included within the scope of the present invention.

I claim:

1. A halophenoxy-alkoxy phosphonate having the formula:

$$(halo)_m\text{-}C_6H_{5-m}\text{-}ORO\text{-}P(=Y)(X)(Z)$$

wherein

R is alkylene having from 1 to 4 carbon atoms;

Y is oxygen or sulfur

X is OH, halo, $$-ORO\text{-}C_6H_{5-m}\text{-}(halo)_m,$$

—ORSROH or OH—NH(R''') (ROH);

Z is —OH, halo, $$-N(R')(R'')$$

or, when X is OH—NH(R''') (ROH), then Z can also be OH—NH(R''') (ROH);

R' is hydrogen or alkyl having from 1 to 4 carbon atoms;

R'' is an alkyl sulfonic acid or a halide or alkali metal salt thereof, where R'' contains not more than 4 carbon atoms;

R''' is hydrogen or —ROH; and m is an integer having a value of from 1 to 5 and wherein at least one of X and Z is other than —OH.

2. The compound of claim 1 having the formula:

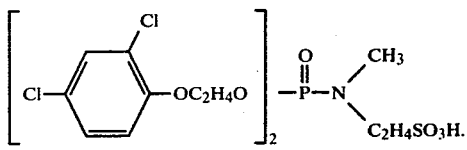

3. The compound of claim 1 having the formula:

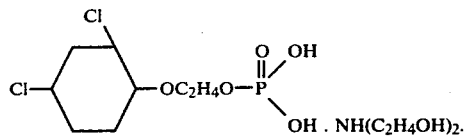

4. The compound of claim 1 having the formula:

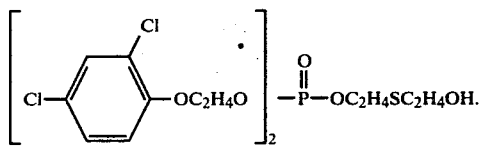

5. The compound of claim 1 having the formula:

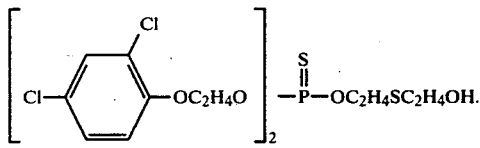

6. A herbicidal composition comprising an effective amount of the compound of claim 1 and an inert carrier therefor.

7. The process for inhibiting the growth of weeds which comprises contacting the plant or plant situs with an effective amount of the compound of claim 1.

8. The composition of claim 6 wherein the compound of claim 1 has the formula:

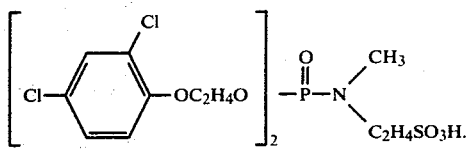

9. The composition of claim 6 wherein the compound of claim 1 has the formula:

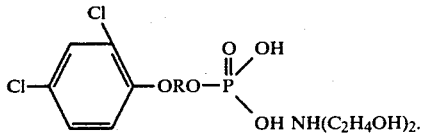

10. The composition of claim 6 wherein the compound of claim 1 has the formula:

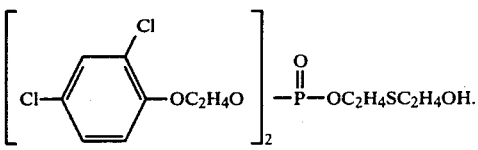

11. The composition of claim 6 wherein the compound of claim 1 has the formula:

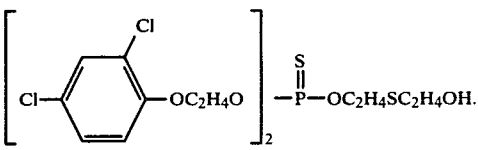

* * * * *